United States Patent
Jokinen

(10) Patent No.: US 8,365,990 B2
(45) Date of Patent: Feb. 5, 2013

(54) METHOD AND SYSTEM FOR REGISTERING OFF-LINE RESPONSE CARDS

(75) Inventor: Tapio Jokinen, Espoo (FI)

(73) Assignee: Medixine Oy, Espoo (FI)

( * ) Notice: Subject to any disclaimer, the term of this patent is extended or adjusted under 35 U.S.C. 154(b) by 427 days.

(21) Appl. No.: 12/798,446

(22) Filed: Apr. 1, 2010

(65) Prior Publication Data

US 2010/0264213 A1   Oct. 21, 2010

(30) Foreign Application Priority Data

Apr. 2, 2009   (FI) ..................... 20095359

(51) Int. Cl.
*G06F 17/00* (2006.01)
*G06K 5/00* (2006.01)
*G06K 7/14* (2006.01)
*G06K 19/06* (2006.01)
*G08B 23/00* (2006.01)
*G06Q 50/00* (2006.01)
*G04F 1/00* (2006.01)

(52) U.S. Cl. ........ 235/380; 235/375; 235/454; 235/492; 340/573.1; 705/3; 702/177

(58) Field of Classification Search .................. 235/375, 235/380, 454, 492; 340/573.1; 705/3; 702/177
See application file for complete search history.

(56) References Cited

U.S. PATENT DOCUMENTS

| 6,085,752 | A  | * | 7/2000 | Kehr et al. .................... 128/897 |
| 7,654,455 | B1 | * | 2/2010 | Bhatti et al. .................. 235/385 |
| 2003/0063524 | A1 | * | 4/2003 | Niemiec et al. ................ 368/10 |
| 2004/0046020 | A1 | * | 3/2004 | Andreasson et al. ......... 235/385 |

FOREIGN PATENT DOCUMENTS

| EP | 1006982 | 6/2000 |
| EP | 1115363 | 7/2001 |
| JP | 2006309740 | 11/2006 |
| WO | WO 2004/023245 | 3/2004 |

* cited by examiner

*Primary Examiner* — Michael G Lee
*Assistant Examiner* — Laura Gudorf
(74) *Attorney, Agent, or Firm* — Ware, Fressola, Van Der Sluys & Adolphson LLP

(57) ABSTRACT

Every off-line response card to be registered comprises a card ID identifying the off-line card uniquely. In the registering process the card ID of a first off-line response card is read and a virtual user ID associated with the card ID of the first off-line response card is obtained. Afterwards, the obtained virtual user ID, for example, can be associated with card IDs of any subsequent off-line response card.

17 Claims, 2 Drawing Sheets

METHOD AND SYSTEM FOR REGISTERING OFF-LINE RESPONSE CARDS

CROSS REFERENCE TO RELATED APPLICATION

This application claims priority under 35 USC §119(e) to Finnish Patent Application No. 20095359 filed on Apr. 2, 2009.

TECHNICAL FIELD OF THE INVENTION

The invention relates to registering off-line response cards.

BACKGROUND OF THE INVENTION

Different kind of enquiries are presented nowadays to users for enquiring (obtaining) their opinions about certain events or experiences, such as asking their opinions about medicines and asking their feelings or conditions after intake of medicines and possible effects of medicines. Some solutions are known from a prior art to follow e.g. medicament dispense or asking some questions. EP 1 006 982 B1 describes a medicament dispense sensing device solution, where sensing elements detect when the medicament is dispensed and an electronic unit registers this with time indication. The medicament dispense sensing device solution is typically integrated with a pharmaceutical package as an off-line response card.

According to the prior art, the user's feedback, answers or other information are determined when the package or off-line response card is returned and the electronic unit is thereafter removed in order to read the registered data thereon for an eventual further evaluation of them. A package is provided with a package identity number for an identity control in connection with the consumed package returned and the electronic unit is removed for e.g. a following systemic evaluation of the patient's data.

There are some disadvantages with the prior art solutions, such as the time consuming way required to evaluate and register the patient's data. It may be that data is read and analysed only from one card and no continuous systematic evaluation is done from plurality of cards. It may also be that when the data is read from the card, the user identity must also be read in order to do statistics. One of the main problems is especially the registering of the cards for a certain user, because according to prior art, the user identity information must also be inputted to the system.

SUMMARY OF THE INVENTION

An object of the invention is to alleviate the drawbacks relating to the known prior art solutions. One object is to provide an easy, fast and reliable way to register off-line response cards so that any statistics related to the cards can be gathered even if the user's identity information is not known.

The invention overcomes the above problems and drawbacks e.g. by providing an arrangement, a method, a terminal and a computer program product disclosed in the independent claims.

According to an embodiment of the invention, each of the off-line response cards to be registered comprises a card ID identifying said off-line card uniquely. In the registering process the card ID of a first off-line response card is read and a virtual user ID associated with said card ID of the first off-line response card is obtained.

In obtaining the virtual user ID, a database may be consulted whether the database already comprises a virtual user ID associated with said card ID of said first off-line response card. If the database does not comprise any virtual user ID association with the card ID in question, a virtual user ID is generated and associated with said card ID of the first off-line response card in order to obtain said virtual user ID for the card. The association is advantageously stored into a memory (memory means), such as into a database so that the generated virtual user ID can be found and obtained afterwards based on the card ID of the off-line response card and vice versa.

However, if the database already comprises association with the card ID, the virtual user ID associated with said card ID can be obtained from the database with said card ID. After obtaining the virtual user ID, any subsequent off-line response card having its own card ID may also be registered for the same virtual user ID and no further virtual user ID is needed for that user. Here the subsequent off-line response card is different from said first off-line response card and is typically any later off-line response card for the user of the original first response card.

After obtaining the virtual user ID, a new subsequent off-line response card may be registered e.g. by reading the subsequent card ID identifying the subsequent card and associating the subsequent card ID of the subsequent off-line response card with said virtual user ID obtained.

According to an embodiment of the invention the user may be asked whether the off-line response card in question is a first card for that user or any subsequent card. If the card is the first card having no association with a virtual user ID, a virtual user ID is generated and associated with the card ID of the first off-line response card in question. However, if the card in question is not a first card but a subsequent card, then there should be a virtual user ID associated with the card ID of any earlier card, such as the first card. In that case the virtual user ID associated with any earlier card, e.g. the first card, may be obtained for example by first reading the card ID of any earlier card and then finding the virtual user ID associated with said card ID of the earlier card, e.g. from the database. The subsequent card may then be registered for that virtual user ID by associating said obtained virtual user ID with the card ID of said subsequent off-line response card.

It should be noted that there may be a plurality of response cards registered for the one virtual user ID dedicated to the user. Thus the virtual user ID may be discovered by using the card ID of any response card ever associated with the virtual user ID. The virtual user ID may be, for example, a uniquely random number with which the card IDs for example can be associated unambiguously. According to an embodiment, other information may also be associated with said virtual user ID, such as information related to the user or his preferences, for example. According to an embodiment, a user interface may be provided via which additional information related for example to the user and/or off-line response card may be stored into the database advantageously in connectable manner with said virtual user ID associated with at least one response card used by the user in question.

According to an embodiment, the off-line response card comprises a plurality of identifiable sensing means, such as electrical sensors implemented by capacitive or resistive means (for example, capacitors and resistors), for example, sensing whether they are influenced for example by a finger so that afterwards it can be determined which sensing means were influenced. Further, the off-line response card also comprises a cover provided with a plurality of questions and at least one choice for each question, where choices are arranged into the cover so that each choice correspond to one sensing element in the off-line response card when the cover is placed on the response card. The card may also comprise a memory (memory means) capable of storing identifying information of influenced sensing means or response information in other words.

According to an embodiment, the cover is an exchangeable or replaceable cover having a unique ID identifying at least the cover type, such as migraine card cover or diabetes card cover, but possibly also questions and choices in it.

According to an embodiment, the identifying information of influenced sensing element stored e.g. into the memory of the cards is also read and advantageously also stored e.g. into the database so that said identifying information can be connected with at least the virtual user ID associated with the card ID of said off-line response card in question. In addition the cover ID (in the embodiment where the cover has an ID) may also be read, whereupon the identifying information of influenced sensing element read may be stored so that said identifying information is also connectable with said cover ID of said off-line response card in question.

Also, influenced choices of said off-line response card and/or cover used on said off-line response card may be determined based on the identifying information of said influenced sensing element and card ID and/or used cover ID. Again response information may be formed based on said determined choices of the off-line response card and/or used cover. The formed response information may also be connectably stored with the virtual user ID associated with the card ID and/or said cover ID of said off-line response card in question.

According to an embodiment, the information from the card, such as card ID, cover ID and/or any memory of the card is read via a short range communication link, such as an RF-link. The card ID, cover ID and/or the memory means of the card may be implemented for example using an RFID-technology. In an advantageous embodiment the memory means are either implemented by an RFID or the memory are in data communication with the RFID so that the memory can be read outside e.g. with an RFID reader. In this way the technological structure of the response card can be kept simple and also inexpensive.

It should be noted that the off-line response card may be used for enquiring (obtaining) different type of information related, for example, to intake or effects of medication, therapy or treatment, feeling of a patient, or opinion about an event or evaluation. Thus the cards or exchangeable covers used in the invention are not only limited to the medical related questions, but by using different questions in the card or cover, every kind of opinions can be asked.

According to an embodiment it is possible to use one off-line response card as a base for different types of exchangeable covers dedicated for different types of questions or enquiries, such as enquiring information about effects of used medicine, therapy or treatment, opinion about an event, such as a TV show, movie, competition, and feeling of a patient for example after medical operation or after taking medicine. In addition the response card may be used for example for a viva voce, evaluation a movie, or for any evaluation of a service event, such as restaurant service or fare.

Especially it should be noted that the final use of the response card can be decided even only just when the response card is taken into the use, because the purpose of the use can be selected by choosing the cover in an appropriate way.

The embodiments of the invention offer clear advantages over the known prior art solutions, such as making the registering process of the cards very easy and fast. In addition the identity of the user can be kept secret if needed. Furthermore when the user has e.g. a medication the doctor may discover information related to the consumed medicines e.g. by reading the card ID of any response card associated with the virtual user ID of the response card used by the user, because the card IDs of every response cards used by the user is associated with the same virtual user ID. Thus the response information of all response cards used by the user can be discovered by the virtual user ID.

The exemplary embodiments of the invention presented in this document are not to be interpreted to pose limitations to the applicability of the appended claims. The verb "to comprise" is used in this document as an open limitation that does not exclude the existence of also unrecited features. The features recited in depending claims are mutually freely combinable unless otherwise explicitly stated.

BRIEF DESCRIPTION OF THE DRAWINGS

Next the invention will be described in greater detail with reference to exemplary embodiments in accordance with the accompanying drawings, in which.

DETAILED DESCRIPTION

Figures 1, 2:
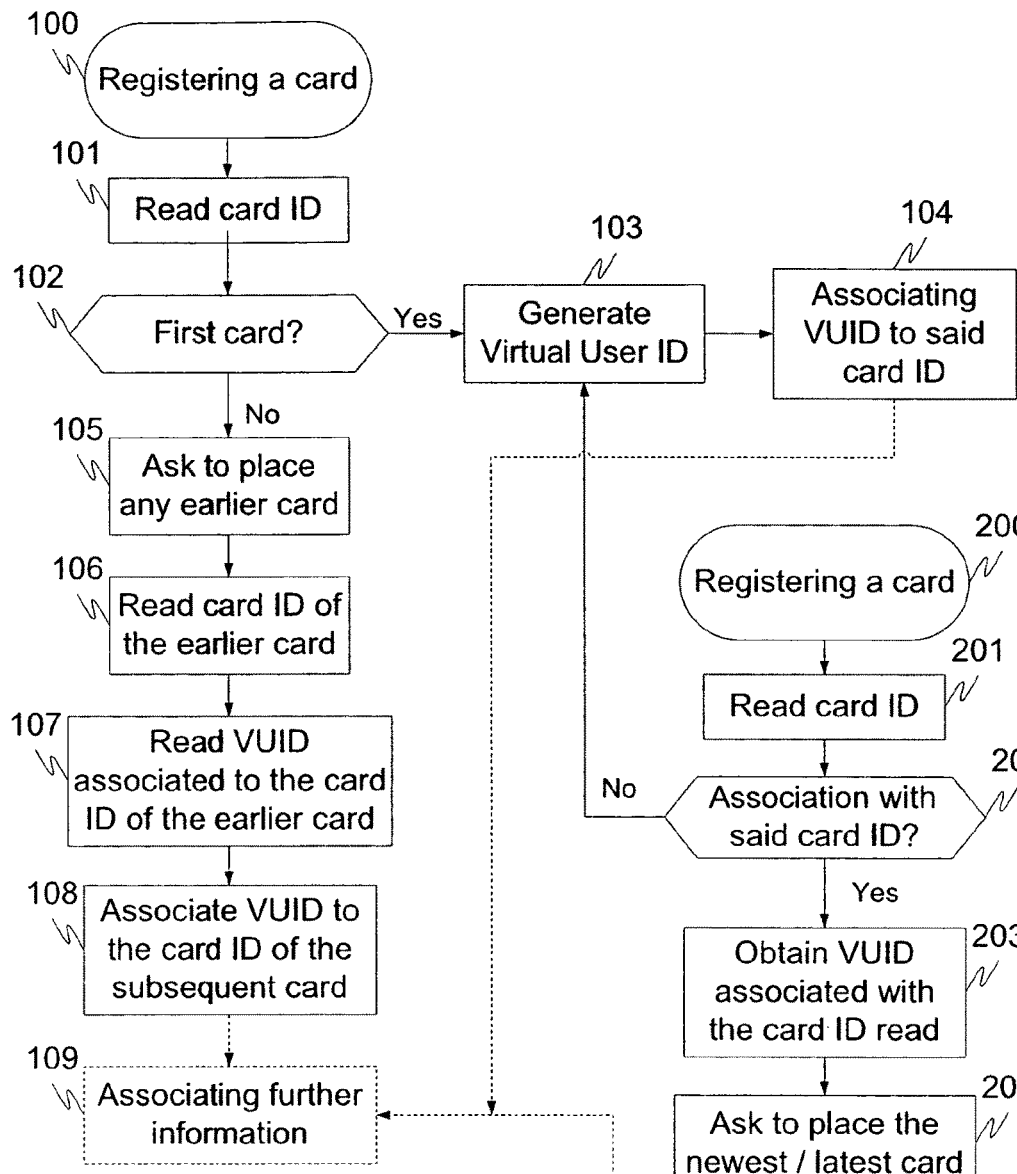
FIG. 1 illustrates an exemplary method for registering an off-line card according to an exemplary embodiment of the invention.
FIG. 2 illustrates another exemplary method for registering an off-line card according to another exemplary embodiment of the invention.

FIG. 1 illustrates an exemplary method 100 for registering an off-line card according to an exemplary embodiment of the invention, where at first in step 101 the card ID is read. In step 102 it is checked whether the card in question is the first one. The checking may be implemented e.g. by asking when the off-line response card is placed near the reading means (reader) whether the off-line response card is a first card or a subsequent card. If the card to be registered is the first one, then there is no virtual user ID (VUID) associated to it, but it is created in step 103, and in step 104 the created VUID is associated with said card ID of the card in question. The association may be done e.g. into a database.

However, if the card is not the first one, but is a subsequent or any later card than the first one, then any earlier card is asked to be placed near the reading means in step 105 in order to read its card ID in step 106, so that the VUID associated with said card ID can be obtained, such as read out from the database in step 107. It should be noted that any one of the earlier cards can be used in steps 105-106, since they all are associated with the same VUID. The obtained VUID is then associated to the card ID of the subsequent card in question in step 108.

In addition, the method may comprise optional step 109, where other information may also be associated to the card ID and/or VUID.

FIG. 2 illustrates another exemplary method 200 for registering an off-line card according to another exemplary embodiment of the invention, which method can be applied especially when the user has already at least one earlier registered card. However, the method is also applicable for the registration of the first cards as well.

In step 201 the card ID is read and in step 202 it is checked whether there is any association with the card ID. If there is the association, the card in question is not the first one but a subsequent card to the card ID of which the VUID has already been associated earlier. If there is the association, the corresponding VUID associated with the card ID of the card in question is obtained in step 203, such as read from the database based on said card ID. After obtaining the VUID, the newest card or any subsequent non-registered card is asked to be placed near the reading means in step 204 so that its card ID can be read in step 205. Then the VUID obtained in step 203 is associated with the card ID of the newest card read in step 205.

However, if there is no association with said card ID in step 202 and the card is the first one, then the VUID is generated for that card in step 102 and associated to said card ID in question in step 103 like in method 100 illustrated in FIG. 1. Also the method 200 may comprise optional step 109, where other information may also be associated to the card ID and/or VUID.

Figure 3:
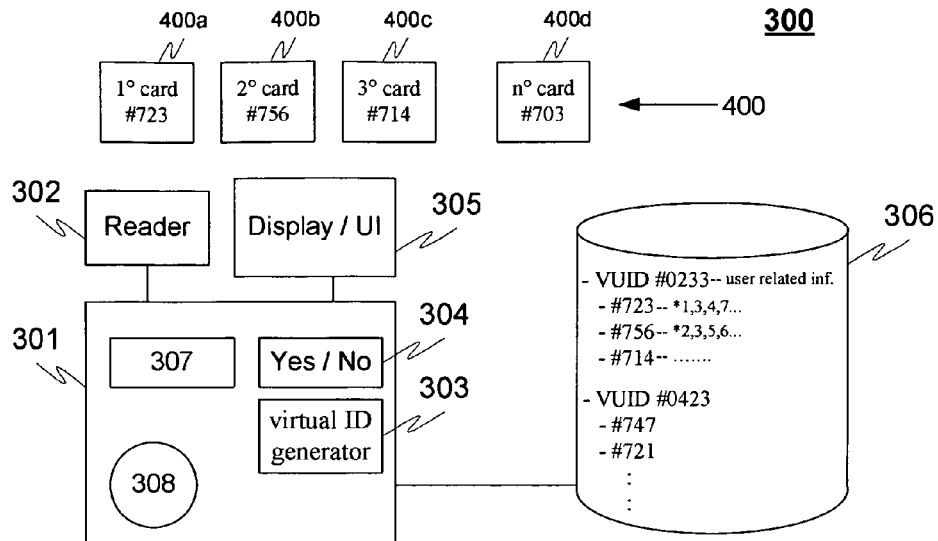
FIG. 3 illustrates an exemplary arrangement for registering an off-line card according to an exemplary embodiment of the invention.

FIG. 3 illustrates an exemplary arrangement 300 for registering an off-line card 400 according to an exemplary embodiment of the invention, where each of the off-line card 400a, 400b, 400c, 400d comprises card ID #723, #756, #714, #703, correspondingly, identifying uniquely each off-line card in question. The arrangement 300 advantageously comprises a terminal 301 having reading means (reader) 302 for reading a card ID of the off-line response card 400 independently whether the card is the first one or any subsequent card. In addition, the terminal also comprises means (virtual ID generator) 303 for obtaining a virtual user ID (VUID) associated with said card ID. If the card is the first one and there is no association, the means 303 are adapted to generate the VUID as well as associate the generated VUID with said card ID in question.

According to an embodiment, the terminal 301 may read the card ID and ask the user e.g. via a user interface device (interface means) 304 whether the card in question is the first one or not. If the card is not the first one, the terminal is adapted to ask e.g. via the user interface, such as a display 305, to place any earlier card near the reader 302 (reading means). The terminal is then adapted to read the card ID of said earlier card, as well as read the VUID associated to the earlier card ID and associate the read VUID to the card ID of the latest one. The terminal may write the association into the database 306 so that the VUID can be found by using any card ID associated with it, or vice versa. The functioning of this embodiment corresponds mainly with the method steps of the method 100 illustrated in FIG. 1.

According to another embodiment the terminal 301 may read the card ID and comprises a checking device (means) 307 for checking e.g. from the database 306 whether there is any association with the card ID. If there is the association, the card in question is not the first one but some subsequent card to the card ID of which the VUID has already been earlier associated. If there is association, the means 307 is adapted to obtain the corresponding VUID associated with the card ID of the card in question, such as read it from the database 306 based on said card ID. After obtaining the VUID, the terminal is adapted to ask the newest card to be placed near the reader 302 so that its card ID can be read. Then the terminal is adapted to associate said obtained VUID with the card ID of the newest card read. The functioning of this embodiment corresponds mainly with the method steps of the method 200 illustrated in FIG. 2.

The arrangement 300 may comprise a user interface means, such as a display and/or keyboard 305 for inputting and also associating further information to the card ID and/or VUID.

According to an embodiment, the terminal 301 may also read indentifying information of influenced sensing of the user off-line response card by reading means 302. Further the terminal may be adapted to store said read information (such as *1, 3, 4, 7, which represent the influenced sensing means) into the database 306 so that said identifying information can be connected with at least the VUID associated with the card ID of said off-line response card in question. In addition the cover ID (in the embodiment where the cover has an ID, such as when the cover is exchangeable cover) may also be read by the terminal, whereupon the identifying information of an influenced sensing element may also be stored so that said identifying information is also connectable with said cover ID of said off-line response card in question.

The arrangement 300 may be adapted to also determine influenced choices of said off-line response card and/or cover used on said off-line response card e.g. based on the identifying information of said influenced sensing element and card ID and/or used cover ID. Again, the arrangement may be adapted to form response information based on said determined choices of the off-line response card and/or used cover, as well as store the formed response information e.g. into the database 306 connectable with the virtual user ID associated with the card ID and/or said cover ID of said off-line response card in question.

At least part of the functioning of the terminal 301 may be implemented by using a computer program product 308 (memory stored with program code for execution by a processor) adapted at least to:

a) read a card ID of a first off-line response card by reading means (reader) (having no association with any virtual user ID),
b) obtain a virtual user ID associated with said card ID of the first off-line response card,
c) read a subsequent card ID identifying another off-line response card, where said subsequent off-line response card is different from said first off-line response card, and
d) associate said subsequent card ID of the subsequent off-line response card with said virtual user ID, when said computer program product 308 is run on the terminal 301.

Figure 4:
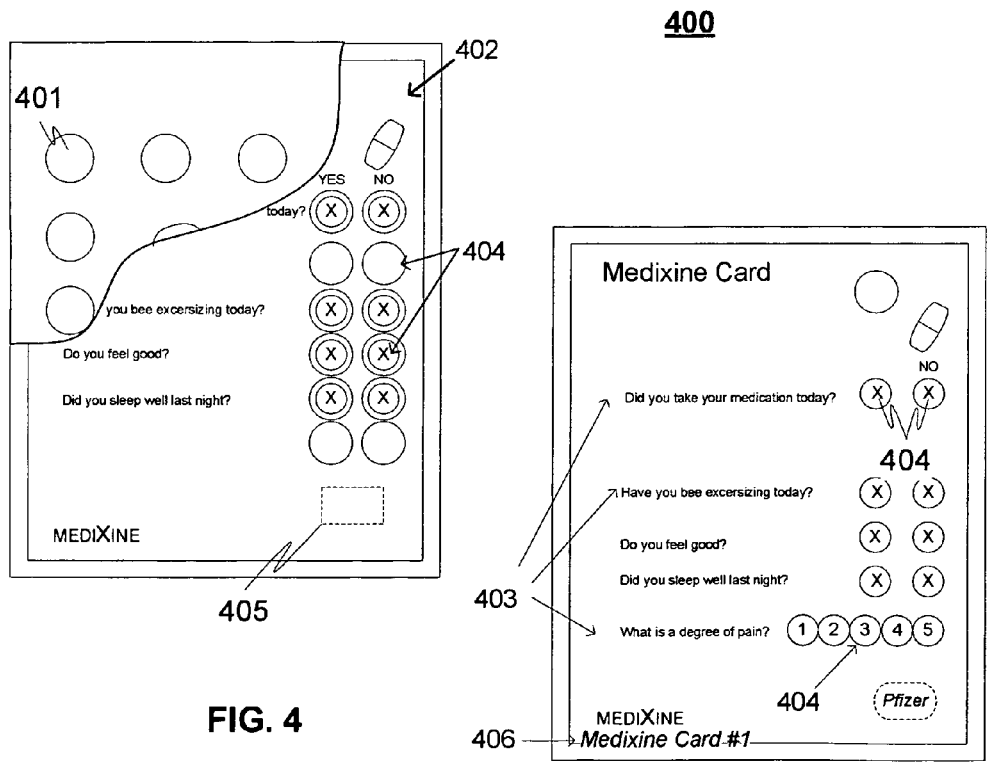
FIG. 4 illustrates an exemplary off-line card according to an exemplary embodiment of the invention.

FIG. 4 illustrates an exemplary off-line response card 400 according to an exemplary embodiment of the invention, where the off-line response card comprises a plurality of identifiable sensing elements 401, and a cover 402 provided with a plurality of questions 403 and at least one choice 404 for each question, where choices are arranged into the cover so that each choice corresponds one sensing element in the off-line response card when the cover is placed on the response card.

The off-line response card 400 may also comprise memory (memory means) 405 being capable of storing indentifying information of influenced sensing means or response information in other words. According to an embodiment the cover 402 is an exchangeable or replaceable cover having a unique ID 406 identifying at least the cover type, such as migraine card or diabetes card, but possibly also questions and choices in it. It should be noted that card ID of one card and/or cover ID of one cover ID may be e.g. #3425676 corresponding e.g. a certain type card, such as migraine card, and that also another card or cover having ID e.g. #324875 may be the same type. Again it should be noted that they can be registered to a same VUID or to different VUID.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims.

What is claimed is:

1. An arrangement for registering off-line response cards, each of the off-line cards comprising a card ID identifying said off-line card wherein, the arrangement is adapted to
    a) a reader configured to read a card ID of a first off-line response card,
    b) a virtual ID generator configured to obtain a virtual user ID associated with said card ID of the first off-line response card,
    c) said reader also configured to read a subsequent card ID identifying another off-line response card, where said subsequent off-line response card is different from said first off-line response card, and
       c1) ask whether the off-line response card is a first card or subsequent card, and if said card is a subsequent card the arrangement is adapted to
           read a card ID of said subsequent off-line response card,
           read the card ID of said first or any other earlier card and thereby obtain a virtual user ID associated with said first or any other earlier card ID, and
    d) said virtual ID generator also configured to associate said subsequent card ID of the subsequent off-line response card with said virtual user ID.

2. The arrangement according to claim 1, wherein the virtual ID generator is also configured to first check from a database whether the database comprises a virtual user ID associated with said card ID of said first off-line response card and generate a virtual user ID if there is no association with said card ID of the first off-line response card and associate said generated virtual user ID with said card ID of the first off-line response card before the reader reads said subsequent card ID.

3. The arrangement according to claim 1, wherein the arrangement is adapted to ask when the off-line response card is placed near the reader whether the off-line response card is a first card or subsequent card, and if said card is the first card, the arrangement is adapted to generate and associate a virtual user ID with said card ID of said first off-line response card.

4. The arrangement according to claim 1, wherein each of the off-line response cards comprises
    a plurality of identifiable sensing elements,
    a cover provided with a plurality of questions and at least one choice for each question, where choices are arranged into the cover so that each choice corresponds to one sensing element in the off-line response card when the cover is placed on the response card, and
    a memory configured to store identifying information of influenced sensing elements,
    and wherein the arrangement is further adapted to:
        read identifying information of influenced sensing elements stored into said memory, and
        store said read identifying information of influenced sensing elements so that said identifying information is connectable with at least the virtual user ID associated of the card ID of said off-line response card in question.

5. The arrangement according to claim 4, wherein said card ID and/or said cover ID is implemented using RFID technology.

6. An arrangement for registering off-line response cards, each of the off-line cards comprising a card ID identifying said off-line card wherein,
    the arrangement is adapted to
        a) a reader configured to read a card ID of a first off-line response card,
        b) a virtual ID generator configured to obtain a virtual user ID associated with said card ID of the first off-line response card,
        c) said reader also configured to read a subsequent card ID identifying another off-line response card, where said subsequent off-line response card is different from said first off-line response card, and
        d) said virtual ID generator also configured to associate said subsequent card ID of the subsequent off-line response card with said virtual user ID, wherein each of the off-line response cards comprises
            a plurality of identifiable sensing elements,
            a cover provided with a plurality of questions and at least one choice for each question, where choices are arranged into the cover so that each choice corresponds to one sensing element in the off-line response card when the cover is placed on the response card, and
            a memory configured to store identifying information of influenced sensing elements,
        and wherein the arrangement is further adapted to:
            read identifying information of influenced sensing elements stored into said memory, and
            store said read identifying information of influenced sensing elements so that said identifying information is connectable with at least the virtual user ID associated of the card ID of said off-line response card in question,
        wherein
            the cover is an exchangeable cover having a unique ID identifying a cover type, identifiable questions and choices,
            and wherein said arrangement is further adapted to
            read said cover ID, and
            store said read identifying information of an influenced sensing element so that said identifying information is connectable in addition with the card ID and/or said cover ID of said off-line response card in question.

7. The arrangement according to claim 4, wherein the arrangement is adapted to determine influenced choices of said off-line response card and/or cover used on said off-line response card based on determined identifying information of said influenced sensing element and card ID and/or used cover ID, and thereby adapted to form response information based on said determined choices of said off-line response card and/or used cover, and store said response information connectable with the virtual user ID associated of the card ID, card ID and/or said cover ID of said off-line response card in question.

8. The arrangement according to claim 1, wherein said reader is adapted to read information from the card via a short range communication link.

9. The arrangement according to claim 1, wherein the arrangement comprises a user interface device via which additional information is stored in a connectable manner with said virtual user ID.

10. The arrangement according to claim 8, wherein said short range communication link uses RF-technology.

11. The arrangement according to claim 8, wherein said card ID is implemented using RFID-technology.

12. The arrangement according to claim 9, wherein the additional information is related to an owner of said off-line response card.

13. A method for registering off-line response cards, each of the off-line cards comprising a card ID identifying said off-line card, wherein the method comprises:
   a) reading a card ID of a first off-line response card,
   b) obtaining a virtual user ID associated with said card ID of the first off-line response card,
   c) reading a subsequent card ID identifying another off-line response card, where said subsequent off-line response card is different from said first off-line response card, and
   d) associating said subsequent card ID of the subsequent off-line response card with said virtual user ID,
   wherein the method comprises asking when the off-line response card is placed near a reader whether the off-line response card is a first card or subsequent card, and if said card is subsequent card the method further comprising:
   reading a card ID of said subsequent off-line response card,
   asking to place the first or any other earlier card than said subsequent card near the reader,
   reading the card ID of said first or any other earlier card and obtaining a virtual user ID associated with said first or any other earlier card ID, and
   associating said virtual user ID with said card ID of said subsequent off-line response card.

14. The method according to claim 13, wherein step b) first comprises checking from a database whether the database comprises a virtual user ID associated with said card ID of said first off-line response card and generating a virtual user ID if there is no association with said card ID of the first off-line response card and associating said generated virtual user ID with said card ID of the first off-line response card before step c).

15. The method according to claim 13, wherein the method comprises asking when the off-line response card is placed near a reader whether the off-line response card is a first card or subsequent card, and if said card is a first card, generating and associating a virtual user ID with said card ID of said first off-line response card.

16. The method according to claim 13, wherein each of the off-line response cards comprises:
   a plurality of identifiable sensing elements,
   a cover provided with a plurality of questions and at least one choice for each question, where choices are arranged into the cover so that each choice corresponds to one sensing element in the off-line response card when the cover is placed on the response card, and
   a memory configured to store identifying information of influenced sensing elements,
   and wherein the method further comprising:
   reading identifying information of influenced sensing elements stored into said memory, and
   storing said read identifying information of influenced sensing elements so that said identifying information is connectable with at least the virtual user ID associated of the card ID of said off-line response card in question.

17. A terminal comprising a computer program product comprising a memory having program code stored thereon for execution by a processor, the computer program product for registering off-line response cards, each of the off-line card comprising a card ID identifying said off-line card, wherein said program code when executed by the processor of the terminal performs:
   a) reading a card ID of a first off-line response card
   b) obtaining a virtual user ID associated with said card ID of the first off-line response card,
   c) reading a subsequent card ID identifying another off-line response card, where said subsequent off-line response card is different from said first off-line response card and
   c1) asking whether the off-line response card is a first card or subsequent card, and if said card is a subsequent card the arrangement is adapted to
      read a card ID of said subsequent off-line response card,
      read the card ID of said first or any other earlier card and thereby obtain a virtual user ID associated with said first or any other earlier card ID, and
   d) associating said subsequent card ID of the subsequent off-line response card with said virtual user ID.

* * * * *